(12) United States Patent
Johnson

(10) Patent No.: US 6,723,404 B2
(45) Date of Patent: Apr. 20, 2004

(54) INHIBITION OF ETHYLENE OXIDE AUTOPOLYMERIZATION

(75) Inventor: Thomas Howard Johnson, Houston, TX (US)

(73) Assignee: Shell Oil Company, Houston, TX (US)

( * ) Notice: Subject to any disclaimer, the term of this patent is extended or adjusted under 35 U.S.C. 154(b) by 83 days.

(21) Appl. No.: 10/091,890

(22) Filed: Mar. 6, 2002

(65) Prior Publication Data
US 2003/0170412 A1 Sep. 11, 2003

(51) Int. Cl.$^7$ .................. B65D 79/00; B65D 81/18
(52) U.S. Cl. .................... 428/35.7; 206/524.4
(58) Field of Search .......................... 428/35.7

(56) References Cited

U.S. PATENT DOCUMENTS 3,142,687 A   7/1964   Goldsmith et al. ......... 260/348

FOREIGN PATENT DOCUMENTS

GB          2027697        2/1980

OTHER PUBLICATIONS

T. H. Baize, "Polymerization of Ethylene Oxide", pp. 903–906.

International Search Report, EPO Appln. No. 03075646, dated Jun. 27, 2003.

"Polymerization of Ethylene Oxide," by T. H. Baize, Industrial and Engineering Chemistry, vol. 53, No. 11, Nov. 1961, pp. 903–906.

Primary Examiner—Sandra M. Nolan

(57) ABSTRACT

A method for reducing the formation of non-volatile residue (NVR) in alkylene oxide, preferably ethylene oxide, comprising contacting the alkylene oxide with fresh electron source material effective to convert ferric ions to ferrous ions. Iron ($Fe^0$), chromium, and a combination thereof are preferred fresh electron source materials, with iron ($Fe^0$) being most preferred.

85 Claims, No Drawings

INHIBITION OF ETHYLENE OXIDE AUTOPOLYMERIZATION

The application relates to a method for reducing the formation of nonvolatile residue (NVR) in ethylene oxide.

BACKGROUND OF THE INVENTION

During storage and/or transport, ethylene oxide (EO) tends to form autopolymerization impurities. The autopolymerization impurities tend to build up as deposits on handling equipment. Because they are not removed from the handling equipment along with the volatile EO, the built up deposits and/or other non-volatile impurities are sometimes called "nonvolatile residue" (NVR).

The presence of NVR renders EO turbid and commercially undesirable. NVR buildup also can cause malfunction of safety release mechanisms, plugging, and general fouling of floats, meter orifices, and other transfer equipment.

Cleaning NVR from EO handling equipment, particularly storage tanks, is dangerous and expensive. The expense is largely due to the relatively prolonged downtime required to clean the tank. Before cleaning an EO storage tank, the EO must be purged from the tank. EPA requirements limit the quantity of EO that can be released into the environment each day. Weeks may be required to slowly purge the storage tank of EO before the storage tank can be cleaned. The process is so costly that small facilities, who may have only one EO storage tank, often replace the storage tank rather than undertake the cleaning process.

It would be much more efficient to prevent the buildup of NVR on the surfaces of EO storage tanks in the first place.

SUMMARY OF THE INVENTION

The present application provides a method for reducing the formation of non-volatile residue (NVR) in alkylene oxides comprising: providing a vessel containing alkylene oxide, said vessel comprising iron; and, contacting said alkylene oxide with a fresh electron source material effective to convert ferric ions to ferrous ions.

The application also provides a storage or transport vessel comprising walls retaining alkylene oxide, said alkylene oxide contacting a fresh electron source material effective to convert ferric ions to ferrous ions.

DETAILED DESCRIPTION

The present application provides a practical approach to counteract the formation of NVR in the handling equipment for alkylene oxides. Suitable alkylene oxides include, but are not necessarily limited to propylene oxide and ethylene oxide. A most preferred alkylene oxide is ethylene oxide. At times, the following description refers only to ethylene oxide, a preferred embodiment. Nevertheless, unless expressly indicated, the description also applies to other alkylene oxides.

The application recognizes that ferric ions ($Fe^{+3}$) are a primary factor in promoting polymerization of alkylene oxides, particularly in handling equipment bearing rust. Rust, or ferric oxide ($Fe_2O_3$), is the reddish corrosion product formed by electrochemical interaction between iron and atmospheric oxygen. It is difficult, if not impossible, to prevent rust from forming on the typical steel equipment used to handle bulk alkylene oxides.

In contrast to ferric ions ($Fe^{+3}$), iron ($Fe^0$) and ferrous ions ($Fe^{+2}$) do not promote polymerization of EO. In fact, the $Fe^0$ present at the surface of a clean carbon steel vessel actually provides a natural immunity to polymer production by providing a fresh electron source with a reduction potential effective to convert ferric ions to ferrous ions. The reduction of ferric ions to ferrous ions by $Fe^0$ is explained in the following electrochemical sequence:

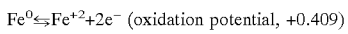

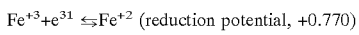

As seen from the foregoing, the conversion of ferric ions ($Fe^{+3}$) to ferrous ions ($Fe^{+2}$) by iron ($Fe^0$) is favored in the electromotive series by greater than 1.17 v. The resulting ferrous ions do not promote EO polymerization.

The presence of $Fe^0$ at the surface of a steel EO vessel provides a natural redox control of EO polymerization—that is, until polymerized EO begins to build up on the internal surface of the steel and to reduce the surface area of the steel exposed to EO. As the surface area of the steel exposed to EO is reduced, the natural inhibition provided by the $Fe^0$ at the vessel surface is reduced, and the rate of NVR formation is increased.

The present application provides the EO with a "fresh electron source material" having a reduction potential effective to reduce ferric ions ($Fe^{+3}$) to ferrous ions ($Fe^{+2}$). As used herein, the term "fresh electron source material" refers to a material that is separate from the original vessel walls. Although a preferred source of electrons is $Fe^0$, preferably carbon steel or stainless steel, the necessary reduction potential may be provided by other electron source materials as well. Suitable electron source materials include, but are not necessarily limited to metals having a one-electron reduction potential of less than +0.77 v vs. a Standard Hydrogen Electrode (SHE). Such metals include, but are not necessarily limited to $Fe^0$ and chromium.

The effectiveness and the life of the fresh electron source material relates to the surface area available to provide electrons for the reduction. Even a rectangular coupon of fresh electron source material has sufficient surface area to drive the reduction, as seen from the examples. However, the process is more efficient if the fresh electron source material has an "expanded surface area."

As used herein, the phrase "expanded surface area" means that the portion of a given weight or volume of material that is exposed to the surrounding environment is greater than the portion that is exposed to the environment using the same weight or volume of material in the form of a rectangular coupon. Porous or filamentous structures are examples of structures with an "expanded surface area." The phrase "expanded surface area" is intended to encompass a variety of structural convolutions which maximize the percentage of the material exposed to the environment, or forming a surface area. Preferably, the fresh electron source material provides a surface area relative to volume of EO of 0.15 ft.$^2$/gallon or more, more preferably at least 0.3 ft.$^2$/gallon or more. Where the electron source material is carbon steel, a more preferred surface area relative to volume of EO is at least 0.45 ft.$^2$/gallon or more.

In a preferred embodiment, the electron source material is a metal sponge or a metal wool, preferably a sponge or wool made of a metal selected from the group consisting of carbon steel and stainless steel.

During the reduction process, electrons from the metal at the surface of the electron source material are transferred to the ferric ions in order to convert them to ferrous ions. The surface of the fresh electron source material eventually is depleted of electrons that readily undergo this reaction, and the depleted electron source material must be replaced in order to continue reducing NVR formation. The fresh electron source material preferably is replaced or replenished on a regular basis, preferably via a removable device, such as a bayonet. Regular replacement of the fresh electron source material will avoid the need to regularly clean the vessel to remove NVR, thereby avoiding the labor and cost involved in regularly cleaning these vessels.

The invention will be better understood with reference to the following examples, which should not be construed as limiting the invention to a particular embodiment. In the following examples, the method used to determine a value for NVR down to a concentration of 2 ppm by weight was as follows:

Determination of NVR

The weight of a 150 ml. clean evaporating dish was tared and 100 ml. of the EO sample was transferred to the clean evaporating dish using a 100 ml. graduated cylinder. The evaporating dish and sample were placed on the steambath and evaporated to dryness under a hood. The dry evaporating dish was removed from the steambath and the condensate was wiped from the outer surface of the dish. The dish was cooled to room temperature in a dessicator for approximately 30 minutes and weighed to the nearest 0.1 mg. After each analysis, the evaporating dish was thoroughly rinsed with distilled water and dried in an oven at 105° C. for a minimum of 30 minutes. Once dried, the dish was placed in a dessicator to cool for at least one hour.

The concentration of NVR in the EO was calculated using the following formula:

$$NVR, \% \ w. = \frac{W2 - W1}{D \times V} \times 100$$

where:

W1=The initial weight of the evaporating dish, without sample (gm).

W2=The final weight of the evaporating dish, after the 100 ml of sample was evaporated (gm).

V=Volume of sample evaporated (100 ml).

D=Density of EO at 10° C. (0.893 g/ml)

The density of EO samples used in the foregoing tests were maintained at 10° C., so the foregoing equation was simplified to:

$$NVR, \% \ w. = \frac{W2 - W1}{0.893}$$

EXAMPLE I

Glass vessels containing EO were exposed to a rusty coupon and the amount of polymer (NVR) formed after a set period of time was measured using the following procedure. Another vessel was treated with a rusty coupon and a clean carbon steel coupon. The results are given in the following Table:

| | NVR Increase, ppm | |
|---|---|---|
| Week | Rust | Rust/cs |
| 1 | 159 | 99 |
| 2 | 279 | 191 |
| 3 | 550 | 351 |

Note:
Initial EO contained 33 ppm NVR

EXAMPLE II

Example I was repeated using 1, 2, and 3 coupons of carbon steel and stainless steel. The following were the results:

| Experiment | Rust g | EO g | Rust ppm | NVR, initial ppm | NVR ppm | NVR, net ppm | (NVR/ppm Rust) ppm |
|---|---|---|---|---|---|---|---|
| Rust/1cs | 0.0075 | 66.5 | 113 | 17 | 87 | 70 | 0.62 |
| Rust/2cs | 0.0090 | 58.6 | 154 | 17 | 81 | 64 | 0.42 |
| Rust/3cs | 0.0085 | 69.3 | 123 | 17 | 48 | 31 | 0.25 |
| Rust/1ss | 0.0060 | 70.8 | 85 | 17 | 81 | 64 | 0.75 |
| Rust/2ss | 0.0068 | 66.5 | 102 | 17 | 44 | 27 | 0.26 |
| Rust/3ss | 0.0073 | 69.2 | 105 | 17 | 46 | 29 | 0.28 |

As seen from the foregoing, the greater the surface area of the clean steel coupons, the greater the inhibition of polymer growth. This was particularly true using the carbon steel coupons.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

What is claimed is:

1. A method for reducing the formation of non-volatile residue in ethylene oxide comprising:
   providing a vessel retaining ethylene oxide comprising ferric ions; and,
   contacting said ethylene oxide with fresh electron source material effective to convert said ferric ions to ferrous ions.

2. The method of claim 1 wherein said fresh electron source material is a metal having a one-electron reduction potential of less than +0.77 vs. a Standard Hydrogen Electrode.

3. The method of claim 1 wherein said fresh electron source material is selected from the group consisting of iron in its zero oxidation state, chromium, and a combination thereof.

4. A method for reducing the formation of non-volatile residue in ethylene oxide comprising:
   providing a vessel retaining ethylene oxide comprising ferric ions; and,
   contacting said ethylene oxide with fresh electron source material comprising iron in its zero oxidation state effective to convert said ferric ions to ferrous ions.

5. The method of claim 1 wherein said fresh electron source material has an expanded surface area.

6. The method of claim 2 wherein said fresh electron source material has an expanded surface area.

7. The method of claim 3 wherein said fresh electron source material has an expanded surface area.

8. The method of claim 4 wherein said fresh electron source material has an expanded surface area.

9. The method of claim 1 wherein said fresh electron source material has a surface area per gallon of ethylene oxide of about 0.15 ft.$^2$ or more.

10. The method of claim 2 wherein said fresh electron source material has a surface area per gallon of ethylene oxide of about 0.15 ft.$^2$ or more.

11. The method of claim 3 wherein said fresh electron source material has a surface area per gallon of ethylene oxide of about 0.15 ft.$^2$ or more.

12. The method of claim 4 wherein said fresh electron source material has a surface area per gallon of ethylene oxide of about 0.15 ft.$^2$ or more.

13. The method of claim 1 wherein said fresh electron source material has a surface area per gallon of ethylene oxide of about 0.30 ft.$^2$ or more.

14. The method of claim 2 wherein said fresh electron source material has a surface area per gallon of ethylene oxide of about 0.30 ft.$^2$ or more.

15. The method of claim 3 wherein said fresh electron source material has a surface area per gallon of ethylene oxide of about 0.30 ft.$^2$ or more.

16. The method of claim 4 wherein said fresh electron source material has a surface area per gallon of ethylene oxide of about 0.30 ft.$^2$ or more.

17. The method of claim 1 wherein said fresh electron source material is selected from the group consisting of a metal sponge and metal wool.

18. The method of claim 2 wherein said fresh electron source material is selected from the group consisting of a metal sponge and metal wool.

19. The method of claim 3 wherein said fresh electron source material is selected from the group consisting of a metal sponge and metal wool.

20. The method of claim 4 wherein said fresh electron source material is selected from the group consisting of a metal sponge and metal wool.

21. A method for reducing the formation of non-volatile residue in alkylene oxides comprising:

providing a vessel retaining alkylene oxide comprising ferric ions; and, contacting said alkylene oxide with fresh electron source material effective to convert said ferric ions to ferrous ions.

22. The method of claim 21 wherein said fresh electron source material is a metal having a one-electron reduction potential of less than +0.77 vs. a Standard Hydrogen Electrode.

23. The method of claim 21 wherein said fresh electron source material is selected from the group consisting of iron in its zero oxidation state, chromium, and a combination thereof.

24. The method of claim 21 wherein said fresh electron source material is iron in its zero oxidation state.

25. The method of claim 21 wherein said fresh electron source material has an expanded surface area.

26. The method of claim 22 wherein said fresh electron source material has an expanded surface area.

27. The method of claim 23 wherein said fresh electron source material has an expanded surface area.

28. The method of claim 24 wherein said fresh electron source material has an expanded surface area.

29. The method of claim 21 wherein said fresh electron source material has a surface area per gallon of alkylene oxide of about 0.15 ft.$^2$ or more.

30. The method of claim 22 wherein said fresh electron source material has a surface area per gallon of alkylene oxide of about 0.15 ft.$^2$ or more.

31. The method of claim 23 wherein said fresh electron source material has a surface area per gallon of alkylene oxide of about 0.15 ft.$^2$ or more.

32. The method of claim 24 wherein said fresh electron source material has a surface area per gallon of alkylene oxide of about 0.15 ft.$^2$ or more.

33. The method of claim 21 wherein said fresh electron source material has a surface area per gallon of alkylene oxide of about 0.30 ft.$^2$ or more.

34. The method of claim 22 wherein said fresh electron source material has a surface area per gallon of alkylene oxide of about 0.30 ft.$^2$ or more.

35. The method of claim 23 wherein said fresh electron source material has a surface area per gallon of alkylene oxide of about 0.30 ft.$^2$ or more.

36. The method of claim 24 wherein said fresh electron source material has a surface area per gallon of alkylene oxide of about 0.30 ft.$^2$ or more.

37. The method of claim 21 wherein said fresh electron source material is selected from the group consisting of a metal sponge and metal wool.

38. The method of claim 22 wherein said fresh electron source material is selected from the group consisting of a metal sponge and metal wool.

39. The method of claim 23 wherein said fresh electron source material is selected from the group consisting of a metal sponge and metal wool.

40. The method of claim 24 wherein said fresh electron source material is selected from the group consisting of a metal sponge and metal wool.

41. A storage or transport vessel comprising walls retaining alkylene oxide comprising ferric ions, said alkylene oxide contacting fresh electron source material effective to convert said ferric ions to ferrous ions.

42. The vessel of claim 41 wherein said fresh electron source material is a metal having a one-electron reduction potential of less than +0.77 vs. a Standard Hydrogen Electrode.

43. The vessel of claim 41 wherein said fresh electron source material is selected from the group consisting of iron in its zero oxidation state, chromium, and a combination thereof.

44. The vessel of claim 41 wherein said fresh electron source material comprises iron in its zero oxidation state.

45. The vessel of claim 41 wherein said fresh electron source material has an expanded surface area.

46. The vessel of claim 42 wherein said fresh electron source material has an expanded surface area.

47. The vessel of claim 43 wherein said fresh electron source material has an expanded surface area.

48. The vessel of claim 44 wherein said fresh electron source material has an expanded surface area.

49. The vessel of claim 41 wherein said fresh electron source material has a surface area per gallon of alkylene oxide of about 0.15 ft.$^2$ or more.

50. The vessel of claim 42 wherein said fresh electron source material has a surface area per gallon of alkylene oxide of about 0.15 ft.$^2$ or more.

51. The vessel of claim 43 wherein said fresh electron source material has a surface area per gallon of alkylene oxide of about 0.15 ft.$^2$ or more.

52. The vessel of claim 44 wherein said fresh electron source material has a surface area per gallon of alkylene oxide of about 0.15 ft.$^2$ or more.

53. The vessel of claim 41 wherein said fresh electron source material has a surface area per gallon of alkylene oxide of about 0.30 ft.$^2$ or more.

54. The vessel of claim 42 wherein said fresh electron source material has a surface area per gallon of alkylene oxide of about 0.30 ft.$^2$ or more.

55. The vessel of claim 43 wherein said fresh electron source material has a surface area per gallon of alkylene oxide of about 0.30 ft.$^2$ or more.

56. The vessel of claim 44 wherein said fresh electron source material has a surface area per gallon of alkylene oxide of about 0.30 ft.$^2$ or more.

57. The vessel of claim 41 wherein said fresh electron source material is selected from the group consisting of a metal sponge and metal wool.

58. The vessel of claim 42 wherein said fresh electron source material is selected from the group consisting of a metal sponge and metal wool.

59. The vessel of claim 43 wherein said fresh electron source material is selected from the group consisting of a metal sponge and metal wool.

60. The vessel of claim 44 wherein said fresh electron source material is selected from the group consisting of a metal sponge and metal wool.

61. A storage or transport vessel retaining ethylene oxide comprising ferric ions, said ethylene oxide contacting fresh electron source material effective to convert said ferric ions to ferrous ions.

62. The vessel of claim 61 wherein said fresh electron source material is a metal having a one-electron reduction potential of less than +0.77 vs. a Standard Hydrogen Electrode.

63. The vessel of claim 61 wherein said fresh electron source material is selected from the group consisting of iron in its zero oxidation state, chromium, and a combination thereof.

64. The vessel of claim 61 wherein said fresh electron source material comprises iron in its zero oxidation state.

65. The vessel of claim 61 wherein said fresh electron source material has an expanded surface area.

66. The vessel of claim 62 wherein said fresh electron source material has an expanded surface area.

67. The vessel of claim 63 wherein said fresh electron source material has an expanded surface area.

68. The vessel of claim 64 wherein said fresh electron source material has an expanded surface area.

69. The vessel of claim 61 wherein said fresh electron source material has a surface area per gallon of alkylene oxide of about 0.15 ft.$^2$ or more.

70. The vessel of claim 62 wherein said fresh electron source material has a surface area per gallon of alkylene oxide of about 0.15 ft.$^2$ or more.

71. The vessel of claim 63 wherein said fresh electron source material has a surface area per gallon of alkylene oxide of about 0.15 ft.$^2$ or more.

72. The vessel of claim 64 wherein said fresh electron source material has a surface area per gallon of alkylene oxide of about 0.15 ft.$^2$ or more.

73. The vessel of claim 61 wherein said fresh electron source material has a surface area per gallon of alkylene oxide of about 0.30 ft.$^2$ or more.

74. The vessel of claim 62 wherein said fresh electron source material has a surface area per gallon of alkylene oxide of about 0.30 ft.$^2$ or more.

75. The vessel of claim 63 wherein said fresh electron source material has a surface area per gallon of alkylene oxide of about 0.30 ft.$^2$ or more.

76. The vessel of claim 64 wherein said fresh electron source material has a surface area per gallon of alkylene oxide of about 0.30 ft.$^2$ or more.

77. The vessel of claim 61 wherein said fresh electron source material is selected from the group consisting of a metal sponge and metal wool.

78. The vessel of claim 62 wherein said fresh electron source material is selected from the group consisting of a metal sponge and metal wool.

79. The vessel of claim 63 wherein said fresh electron source material is selected from the group consisting of a metal sponge and metal wool.

80. The vessel of claim 64 wherein said fresh electron source material is selected from the group consisting of a metal sponge and metal wool.

81. The vessel of claim 1 wherein said fresh electron source material is carbon steel having a surface area per gallon of ethylene oxide of about 0.45 ft.$^2$ or more.

82. The vessel of claim 4 wherein said fresh electron source material is carbon steel having a surface area per gallon of ethylene oxide of about 0.45 ft.$^2$ or more.

83. The vessel of claim 21 wherein said fresh electron source material is carbon steel having a surface area per gallon of alkylene oxide of about 0.45 ft.$^2$ or more.

84. The vessel of claim 41 wherein said fresh electron source material is carbon steel having a surface area per gallon of alkylene oxide of about 0.45 ft.$^2$ or more.

85. The vessel of claim 61 wherein said fresh electron source material is carbon steel having a surface area per gallon of ethylene oxide of about 0.45 ft.$^2$ or more.

* * * * *